US006165123A

United States Patent [19]
Thompson

[11] Patent Number: 6,165,123
[45] Date of Patent: Dec. 26, 2000

[54] CONTROLLABLE MULTI-DIRECTIONAL POSITIONING SYSTEM

[75] Inventor: Robert Lee Thompson, Rogers, Ark.

[73] Assignee: Pinotage LLC, Fayetteville, Ark.

[21] Appl. No.: 09/141,201

[22] Filed: Aug. 27, 1998

Related U.S. Application Data

[60] Provisional application No. 60/057,057, Aug. 27, 1997.

[51] Int. Cl.⁷ .................................................. A61B 1/015
[52] U.S. Cl. ........................ 600/152; 600/114; 600/159; 600/143
[58] Field of Search ................................... 600/102, 114, 600/115, 116, 121, 144, 139, 143, 152, 156, 159; 604/281, 282

[56] References Cited

U.S. PATENT DOCUMENTS

| | | |
|---|---|---|
| 3,557,780 | 1/1971 | Sato . |
| 4,575,185 | 3/1986 | Wentzell et al. .................. 600/152 |
| 4,826,281 | 5/1989 | Ohkawa et al. .................. 600/101 |
| 4,892,099 | 1/1990 | Ohkawa et al. .................. 600/116 |
| 4,893,613 | 1/1990 | Hake .................................. 600/152 |
| 4,906,230 | 3/1990 | Maloney et al. . |
| 4,947,827 | 8/1990 | Opie et al. . |
| 4,971,033 | 11/1990 | Shlers ................................ 600/182 |
| 4,976,191 | 12/1990 | Suzumori et al. .................. 92/48 |
| 5,018,506 | 5/1991 | Dana et al. . |
| 5,019,121 | 5/1991 | Krauter . |
| 5,025,778 | 6/1991 | Silverstein et al. . |
| 5,026,366 | 6/1991 | Leckrone ........................... 606/7 |
| 5,096,292 | 3/1992 | Sakamoto et al. ................ 600/101 |
| 5,140,975 | 8/1992 | Krauter ............................. 600/152 |
| 5,166,787 | 11/1992 | Irion . |
| 5,171,305 | 12/1992 | Schickling et al. .............. 604/271 |
| 5,188,094 | 2/1993 | Adair ................................. 600/122 |
| 5,203,319 | 4/1993 | Danna et al. ..................... 600/152 |
| 5,257,618 | 11/1993 | Kondo . |
| 5,271,381 | 12/1993 | Ailinger et al. . |
| 5,342,299 | 8/1994 | Snoke et al. . |
| 5,353,783 | 10/1994 | Nakao et al. ..................... 600/156 |
| 5,368,015 | 11/1994 | Wilk . |
| 5,447,149 | 9/1995 | Kikawada et al. ................ 600/229 |
| 5,489,256 | 2/1996 | Adair . |
| 5,531,664 | 7/1996 | Adachi et al. . |
| 5,558,619 | 9/1996 | Kami et al. . |
| 5,591,119 | 1/1997 | Adair ................................. 600/112 |
| 5,619,993 | 4/1997 | Lee .................................... 600/146 |
| 5,626,553 | 5/1997 | Frassica et al. . |
| 5,647,840 | 7/1997 | D'Amelio et al. ................ 600/176 |
| 5,704,892 | 1/1998 | Adair ................................. 600/121 |

FOREIGN PATENT DOCUMENTS

| | | | |
|---|---|---|---|
| 41 36 737 | 5/1992 | Germany . | |
| 714-063 | 2/1980 | U.S.S.R. .......................... | 600/152 |

OTHER PUBLICATIONS

International Search Report issued from International Application No.: PCT/US98/17783, mailed on Nov. 27, 1998.

*Primary Examiner*—John P. Leubecker
*Attorney, Agent, or Firm*—Wolf, Greenfield & Sacks P.C.

[57] ABSTRACT

A surgical positioning device that includes a body having a first un-stressed configuration and at least one fluid channel to receive a fluid. The at least one fluid channel is constructed and arranged to transform the body of the surgical positioning device from the first un-stressed configuration to a second configuration when fluid is forced into the at least one fluid channel. The surgical positioning device can include one or more working channels that permit surgical devices to be remotely positioned by the surgical positioning device by adjusting an amount of fluid forced into the at least one fluid channel.

4 Claims, 6 Drawing Sheets

CONTROLLABLE MULTI-DIRECTIONAL POSITIONING SYSTEM

This application claims priority under 35 U.S.C.§ 119 (e) to U.S. provisional patent application serial No. 60/057,057, entitled "Controllable Multi-Directional Positioning System", filed Aug. 27, 1997, which is incorporated herein by reference in its entirety.

BACKGROUND OF THE INVENTION

1. Field Of The Invention

The present invention is directed to a remotely controlled, multi-directional, positioning system, and more particularly, to a multi-directional positioning system that includes a device that can be controllably positioned with a remote pressure control system.

2. Discussion Of The Related Art

In a wide variety of technological disciplines, a positioning device is used to position the working end of an instrument at a location that would be otherwise inaccessible to the instrument. For example, in the medical field, a cannula can be inserted into a body of a patient to guide the working end (e.g., the distal end) of a surgical instrument, such as a retractor, a catheter, an endoscope or other imaging device, etc., to a particular location within the body of the patient. Typically, the cannula is a rigid structure that guides the surgical instrument in only a single direction along the longitudinal axis of the cannula. When the position of the working end of the surgical instrument needs to be moved to a new position that is not along the longitudinal axis of the cannula, the position of the cannula, and thus the position of the working end of the surgical instrument, is adjusted to orient the longitudinal axis of the cannula to point to the new position.

SUMMARY OF THE INVENTION

According to one embodiment of the present invention, a surgical positioning device is provided. The surgical positioning device includes a body having a first un-stressed configuration and at least one fluid channel to receive a fluid. The at least one fluid channel is constructed and arranged to transform the body of the surgical positioning device from the first un-stressed configuration to a second configuration when fluid is forced into the at least one fluid channel.

According to another embodiment of the present invention, a surgical method is provided for a positioning device that includes at least one fluid channel for receiving a fluid. The method includes steps of inserting a portion of the positioning device into a patient's body, and adjusting an amount of fluid in the at least one fluid channel to alter a configuration of the portion of the positioning device that is inside the patient's body.

According to another embodiment of the present invention, a surgical system is provided. The surgical system includes a positioning device and an endoscope. The positioning device includes a body having a first un-stressed configuration and at least one fluid channel to receive a fluid. The fluid channel is constructed and arranged to transform the body of the positioning device from the first configuration to the second configuration when fluid is inserted into the at least one fluid channel. The body of the positioning device includes a scope-receiving channel that extends between a proximal end of the positioning device and a distal end of the positioning device. The endoscope has a distal end that is constructed and arranged to be disposed within the scope-receiving channel of the positioning device.

According to a further embodiment of the present invention, a positioning device is provided. The positioning device includes a body having a first un-stressed configuration and at least one fluid channel to receive a fluid. The at least one fluid channel is constructed and arranged to transform the body of the positioning device from the first un-stressed configuration to a second configuration when fluid is forced into the at least one fluid channel.

According to another embodiment, a pressure control system is provided for use with a positioning device having a first un-stressed configuration and at least one fluid channel to receive a fluid. The at least one fluid channel is constructed and arranged to transform the body of the positioning device from the first un-stressed configuration to a second configuration when the fluid is inserted into the at least one fluid channel. The pressure control system includes a body having at least one reservoir for storing the fluid and an opening that is in fluid communication with the reservoir, and a control, coupled to the opening, that allows the fluid to pass through the opening and return to the reservoir when the control is in a first position.

BRIEF DESCRIPTION OF THE DRAWINGS

Illustrative embodiments of the present invention are described by way of example with reference to the accompanying drawings, in which:

FIG. 5 is a perspective view of a pressure control system according to another embodiment of the present invention that is also suitable for use with the positioning device of FIG. 1;

DETAILED DESCRIPTION

Figure 1:
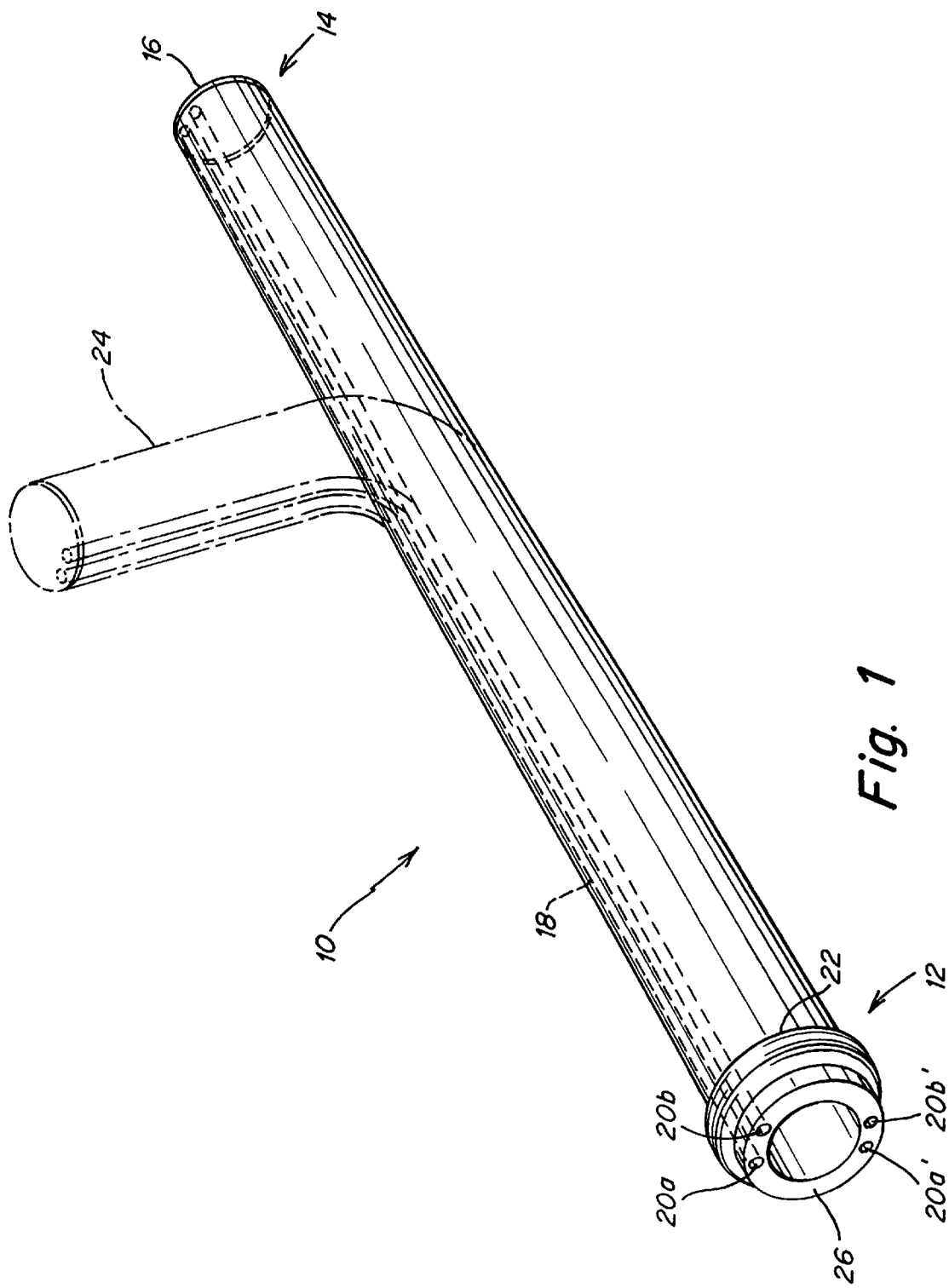
FIG. 1 is a perspective view of a controllable directional positioning device according to one embodiment of the present invention.

Embodiments of the present invention are directed to a remotely controlled, multidirectional, positioning system that can be used to remotely control a position of a working end (e.g., the distal end) of an instrument. In one embodiment of the present invention, the remotely controlled, multi-directional positioning system includes a positioning device having a distal end that is controllably positioned in response to a remote pressure control system that is connected to the other end (e.g., the proximal end) of the device. In this manner, the distal end of an instrument or tool that is inserted into a body of the device can be remotely and controllably positioned. The body, which may be tubular or any other suitable shape, can be manufactured from a flexible material, such as a plastic (e.g., polyethylene) so that it has a curved shape in its unstressed or rest position. The device includes at least one longitudinally oriented fluid channel, connected to the pressure control system at one end (e.g., the proximal end) and closed at the other, that is constructed and arranged to transform the body of the positioning device from a first un-stressed configuration to a second configuration when fluid is forced into the at least one fluid channel.

When a fluid (e.g., a liquid or gas) is forced into the fluid channel, the pressure of the fluid causes the body to straighten, thereby changing the position of the distal end of the device. It should be appreciated that when the body is tubular in shape and retains at least some of its curvature, rotation of the body causes the distal end to sweep in an arc, the size of which is dependent on the amount of curvature of the body. By varying the amount of fluid in the fluid channel, the amount of curvature of the body can be controlled. Thus, by rotating the body and varying the amount of fluid in the fluid channel, a wide range of possible positions of the distal end of the device are possible. The body of the device can optionally have physical features (e.g., scallops) formed therein in the area of the curve to facilitate straightening of the body.

The distal end of the device can be sealed, open, or partially sealed and partially open. When the distal end of the device is sealed, the interior of the device can be used to remotely position an instrument and shield the instrument from contact with the environment outside the device. For example, in one embodiment of the present invention, the positioning system can be used to implement a remotely controlled multi-directional camera system that permits remote viewing of an object, even when the object is only accessible via a confined and/or convoluted passageway. The camera system can include an imaging subsystem, for example, a charge-coupled device ("CCD") and lens, and a light source, located at the working end of the positioning device. To permit the imaging sub-system to view objects that are located outside the device, the seal at the distal end of the device can be transparent. Because the imaging sub-system is separated from the environment outside the device the multi-directional camera system can be used in environments that would otherwise interfere with, or degrade the operation of the imaging sub-system. By manipulating the positioning system in the manner described above, the imaging sub-system can be positioned to view an object that is remotely disposed from the control end of the device, and possibly separated therefrom by a curved or convoluted path or passageway. One application for the remotely controllable camera system is to implement an endoscope used for viewing the interior of a patient's body (e.g., during a surgical procedure). The patient can be a human, or an animal. However, as discussed further below, a number of other applications for the remotely controllable positioning system are possible.

In another embodiment of the present invention, the positioning device has a working channel that is open at both ends so that an instrument or tool can be guided through the working channel. The distal end of the device can optionally have a feature for enabling physical attachment of the instrument. By adjusting the amount of fluid in the fluid channel, the working end of the device, and consequently the instrument disposed in the body of the device, can be positioned at any number of various positions. It should be appreciated that the flexible positioning body and a flexible instrument disposed therein can be guided through a curved or convoluted path into locations that would be inaccessible by a rigid instrument. Furthermore, because the body has a certain amount of rigidity, and because the rigidity of the body can be altered by varying the amount of fluid in the fluid channel, the body and a flexible instrument disposed therein can be guided through convoluted paths much more easily than the flexible instrument alone.

In a further embodiment, the positioning device can include a first channel that is open at the proximal end of the first channel and sealed at the distal end, and a second channel that is open at both proximal and distal ends. The first channel can receive a first instrument that is shielded from contact with the environment outside the device, while the second channel can receive a second instrument that is not so shielded. For example, in one embodiment, an endoscope or other viewing device can be inserted into the first channel, and another surgical instrument, such as a retractor, can be inserted into the second channel. Because the endoscope is shielded from the outside environment, the endoscope need not be sterile. In a further embodiment, other working channels can be provided in the device to provide for suction or irrigation, or for other purposes.

The positioning device can be provided with any desired dimensions to permit a wide variety of instruments to be used, or to allow multiple instruments to be passed through the working channel at the same time. Alternatively, the positioning device can be dimensioned to accommodate a particular instrument. For example, for surgical procedures in a patient's body, the working channel of the positioning device can be adapted to accommodate a surgical instrument, a light source and a viewing instrument, such as a CCD camera, that enables the surgeon to view the surgical site within the body. However, it should be understood that the present invention can be used with any viewing instrument, as well as other types of medical instruments.

FIG. 1 represents an illustrative implementation of a positioning device 10. For the embodiment of the invention directed to the implementation of a remotely controllable camera system, wherein a viewing system is inserted into the positioning device, the positioning device 10 serves as a housing for the camera system. The tubular positioning device 10 (which is circular in cross-section in FIG. 1 but can take other shapes) has a proximal end 12 and a distal end 14. The positioning device 10 can be formed from a flexible material such as a plastic (e.g., polyethylene), although other materials may be also be used.

The distal end of the device 10 is sealed with a transparent seal 16 which may be made of any suitable material including plastic or glass. Preferably, the seal 16 is optically clear to prevent interference with the generation of a clear image by the camera system. The seal 16 seals the interior of the positional device 10 from contact with the external environment. Thus, when used in an endoscopic viewing instrument for insertion into a patient's body, the device 10 and seal 16 prevent the camera disposed therein from being exposed to the body, so that the optical components need not be sterilized. This freedom from required sterilization avoids the costs associated with sterilization (e.g., the cost of sterilization equipment, the cost of the fluid or gas used in sterilization, the environmental costs associated with storing, using, and disposing of such materials, etc.), reduces wear on the camera system, and allows the same camera to be used sequentially on different patients, thus eliminating the need for a doctor to purchase multiple cameras for use on multiple patients consecutively.

As discussed above, within the positioning device 10 is at least one longitudinally oriented fluid channel 18 that terminates at the distal end 14 of the housing 10. The fluid channel 18 can be formed in any of numerous way. In one embodiment, the channel 18 is formed integrally with the body of the positioning device 10 and from the same material. Because the fluid channel 18 is formed integrally with the body of the positioning device 10, both the inner and the outer surfaces of the device 10 can be smooth. This facilitates the insertion, positioning, and removal of the positioning device 10 within convoluted passageways, and facilitates the insertion and removal of instruments within the body of the device 10. Of course, it should be appreciated that fluid channel 18 may alternatively be disposed on the inner surface, or the outer surface of the device 10.

As shown in the embodiment of FIG. 1, the at least one fluid channel 18 can include a plurality of fluid channels to facilitate the straightening of the body of the positioning device 10, although a single channel can also be used. At the proximal end 12 of the positioning device 10, the fluid channels 18 merge at a neck 26. In the neck 26 are a pair of openings 20a and 20b into which the fluid may flow or ebb. For example, opening 20a may be used to force a liquid or gas into the fluid channels 18, and opening 20b may be used to recover liquid or gas ebbing from the fluid channels 18, or vice versa. Alternatively, a single port to the fluid channels can be provided for the insertion and removal of the fluid. A second pair of openings 20a' and 20b' can also be provided for reasons discussed below.

In the resting state when no gas or fluid is forced (e.g., injected, pumped, etc.) into the fluid channels 18, the positioning device 10 has a curved shaped similar to phantom portion 24 shown in dotted line in FIG. 1. However, when fluid is forced into the fluid channels 18, the pressure of the fluid begins to straighten the positioning device 10. The degree of flex, and thus the direction of view through the transparent seal 16, is adjusted by regulating the pressure of the fluid in the fluid channels 18. Moreover, by rotating the positioning device 10, any desired direction of view can be obtained. In the embodiment of FIG. 1, the plurality of longitudinal fluid channels 18 are only oriented along the inner portion of the curve of the positioning device 10. However, the fluid channels 18 may alternatively be oriented along the outer portion of the curve, or may be longitudinally oriented along the positioning device 10 in a circumferential placement. Furthermore, the fluid channels 18 may also be oriented in a spiral along the length of the positioning device 10. In this manner, by regulating the pressure of the fluid in the fluid channels 18, a degree of rotation of the distal end of the device 10 relative to the proximal end of the device can be obtained.

In the embodiment of the invention shown in FIG. 1, the positioning device 10 includes a sterile drape 22. The drape 22 may be provided when the positioning device is used in a surgical or sterile environment. For example, when the positioning device 10 is used to position an endoscope for viewing the interior of a patient's body, the sterile drape 22 can be unrolled over any non-sterile components of the system (e.g., portions of the camera) that are within the sterile operating field. Thus, because none of the components of the camera system contact the sterile operating field (being enclosed within the sealed housing 10 or the drape 22), the camera system need not be sterilized. The positioning device 10 may be sterile and disposable, or alternatively, may be made from a material that may be sterilized to allow for multiple uses.

In one embodiment of the present invention, the sterile drape 22 is bonded to the sterile positioning device 10 and the device and drape are provided as a single unit that may be used once and discarded. The drape 22 may be formed from any suitable material such as latex, or more preferably from plastic, as some people are allergic to latex.

When the positioning device 10 is used within a human or animal patient, the fluid that is used to control the direction of view through the seal 16 is preferably selected to be a fluid that will not be harmful to the patient in the event of leakage (e.g, carbon dioxide gas or a sterile saline solution). It should be appreciated that for other applications that are not within the body and not in a sterile field, any of a number of other types of fluids can be employed. For those non-medical applications, the fluid should be selected to be harmless in the event of leakage for the particular application.

Figure 2:
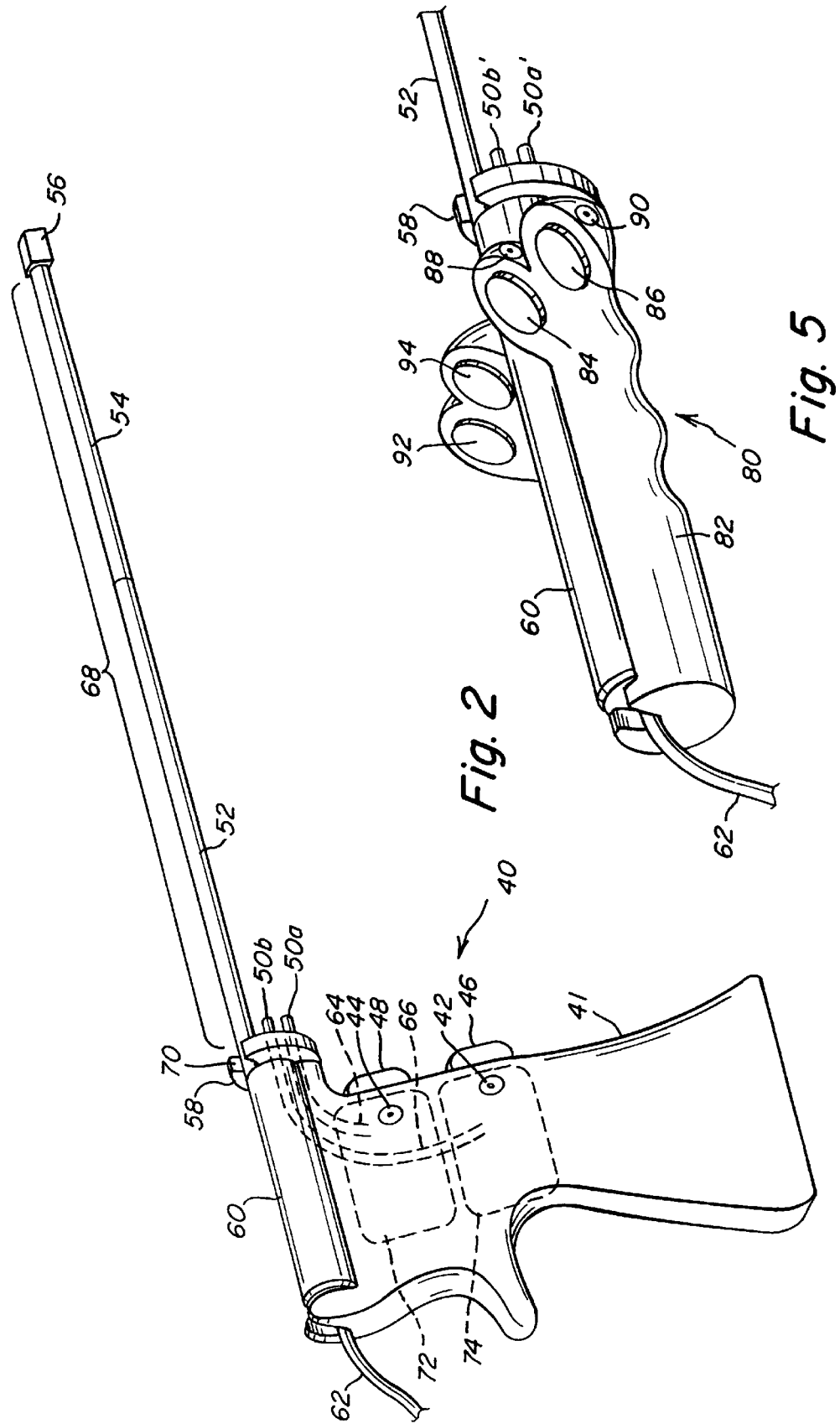
FIG. 2 is a perspective view of a pressure control system according to another embodiment of the present invention that is suitable for use with the positioning device of FIG. 1 to form a positioning system.

FIG. 2 is a perspective view of a camera system mounted to a pressure control system 40 that can be used to control the positioning device 10 according to one embodiment of the present invention. The positioning device 10 is not shown in FIG. 2. The pressure control system 40 includes a pistol grip 41 that can be used by left-handed or right-handed persons equally well. For surgical applications, the pistol grip 41 can be made of a material that is sterile and is readily and economically disposable. Alternatively, it may be made of a material that can be sterilized and reused.

The pistol grip 41 contains at least one reservoir for storing the fluid that is to be forced into the fluid channels 18 of the positioning device 10. In the embodiment depicted in FIG. 2, two distinct reservoirs 72, 74 are contained within the pistol grip 41 for storing fluid. The first reservoir 72 stores a sterile fluid (e.g., saline solution) to be forced into the fluid channels 18, while the second reservoir 74 stores the sterile fluid that is allowed to ebb from the fluid channels 18. The first reservoir 72 is accessed via orifice 44 which allows the fluid to be inserted in a sterile environment into the first reservoir 72, for example, via a hypo-dermic needle, while the second reservoir 74 is accessed via orifice 42 which allows the fluid to be removed from the second reservoir 74 in the same fashion. Fluid is forced into the fluid channels 18 via body 64 by actuating pump trigger 48, while fluid is removed from the fluid channels 18 via body 66 by actuating release trigger 46. Body 64 ends in tip 50a and connects to opening 20a (FIG. 1) in the positioning device 10, while body 66 ends in tip 50b and connects to opening 20b (FIG. 1) in the positioning device 10. The openings 20a' and 20b' (FIG. 1) are used by an alternate pressure control system shown in FIG. 5, and are covered by plate 58 of the pistol grip 41 in a fluid tight manner. Although, the openings 20a' and 20b' are not necessary for use with the pressure control system of FIG. 2, providing them advantageously enables a single camera housing 10 to be used with different types of pressure control systems. When pump trigger 48 is actuated, pressure in reservoir 72 is increased, forcing fluid past a one way valve (not shown) in tip 50a. Alternatively, when release trigger 46 is actuated, a one way valve in tip 50b permits the fluid to ebb into reservoir 74.

In an alternate embodiment, the pistol grip 41 can include only a single reservoir that is accessible by only one orifice such as orifice 42 or 44. In this embodiment, a valve is provided whereby actuation of the pump trigger 48 increases the pressure in the single reservoir and forces fluid past the valve into one of tips 50a or 50b, while actuation of the release trigger 46 actuates the valve to permit fluid or gas to ebb back into the single reservoir.

The camera system illustrated in FIG. 2 includes a camera control unit (CCU) 60, a shaft 68, and an imaging subsystem 56. The shaft 68 of the camera system securely rests within notch 70 of plate 58 of the pressure control system 40, so that the device is conveniently handled as a single unit. However, it should be appreciated that the present invention is not limited in this respect, and that the camera system need not be mountable to the pressure control system.

Imaging sub-system 56 includes a charge-coupled device ("CCD") camera that, in operational use, is mounted adjacent the transparent seal 16 of the positioning device 10. The imaging sub-system 56 further includes a lens (not shown) that is coupled to the CCD and a light source. Electronic signals of images that are processed by the imaging sub-system 56 are transmitted to the camera control unit 60 via a shaft 68, and then, from camera control unit 60 via cable 62 to a system (not shown) for storage and/or display. The storage and display system can be an all digital system, although other types of storage and display systems can also be used. The shaft 68 includes a rigid portion 52, and a somewhat shorter flexible portion 54 that is attached to the imaging sub-system. In one embodiment for use in the endoscopic/surgical application, the flexible portion 54 is approximately five inches long and is formed by a "flex circuit" while the longer rigid portion 52 is approximately nine inches long. This embodiment is particularly well suited to endoscopic applications where motion in only the distal end of the endoscope is required. Of course, other dimensions and varying degrees of stiffness may be used for other applications. When the camera control system is in use in an environment that requires a sterile field, the positioning device 10 encloses the imaging sub-system 56 and the shaft 68, while the sterile drape 22 covers the camera control unit 60 and the cable 62. The pair of openings 20a, 20b in the neck of the positioning device 10 are aligned with tips 50a and 50b, and the neck 26 of the positioning device 10 is secured to plate 58. The positioning device 10 and the sterile drape 22 protect the camera system from contaminating the patient and vice versa, allowing the camera system to be re-used without sterilization.

Figure 3:
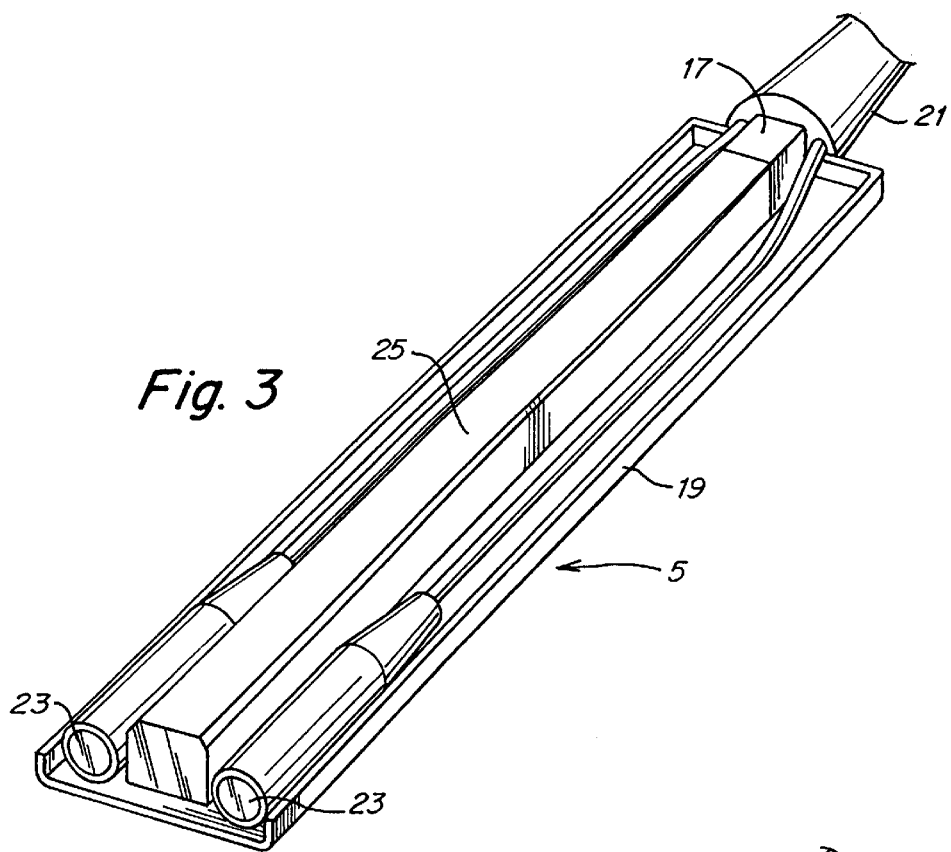
FIG. 3 is a perspective view of an imaging sub-system that is suitable for use with the positioning system of the present invention to form a positionable camera system.

FIG. 3 is a perspective view of an imaging sub-system that is suitable for use with embodiments of the present invention. This imaging sub-system is described merely for illustrative purposes and it should be appreciated that the present invention is not limited to use with any particular type of imaging sub-system. As shown in FIG. 3, the imaging sub-system 5 includes a CCD camera 17 mounted adjacent to the proximal end of an elongated sled 19. The camera 17 is connected to the CCU 60 (FIG. 2) by a camera cable 21. As noted above, camera cable 21 may be formed by a flex circuit (e.g., 54 in FIG. 2). The cable 21 also includes conductors which extend to and provide electrical power to a pair of high-hinensity lights 23 mounted at the distal end of the sled 19. Preferably, the light source (e.g., lights 23) are capable of generating sufficient heat energy so that the inside surface of the transparent seal 16 (FIG. 1) resists fogging when inserted into warm and moist environments, such as a body cavity.

A fiber optic bundle 25 extends proximally from the distal end of the sled 19 and is optically connected to the camera 17. The fiber optic bundle 25 carries images to the camera 17. For example, a single optical fiber or a bundle of optical fibers can be disposed at the distal end of the device and be arranged to transmit the image to the CCD camera 17, which can be positioned at the proximal end of the device. A single (relatively larger) fiber can be used to increase the field of view and to avoid a faceted image. Locating the CCD camera 17 at the proximal end of the sled 19 and using a single optical fiber or fiber optic bundle 25 to optically connect the CCD camera 17 to the distal end of the sled 19 minimizes the crosssectional area of the distal end of the imaging sub-system 5. This allows the remotely controllable camera system to be used in applications wherein a small camera system is desired, as it permits the camera control system to have a narrower distal end. As noted above, the imaging sub-system 5 can also include a lens (not shown) that is typically mounted adjacent the CCD camera 17. Further details of one possible construction and arrangement of a CCD camera and lens assembly is described in Applicant's co-pending U.S. patent application Ser. No. 09/126,368, filed Jul. 30, 1998, and entitled, "Imaging Device", which is incorporated herein by reference.

Figure 4:
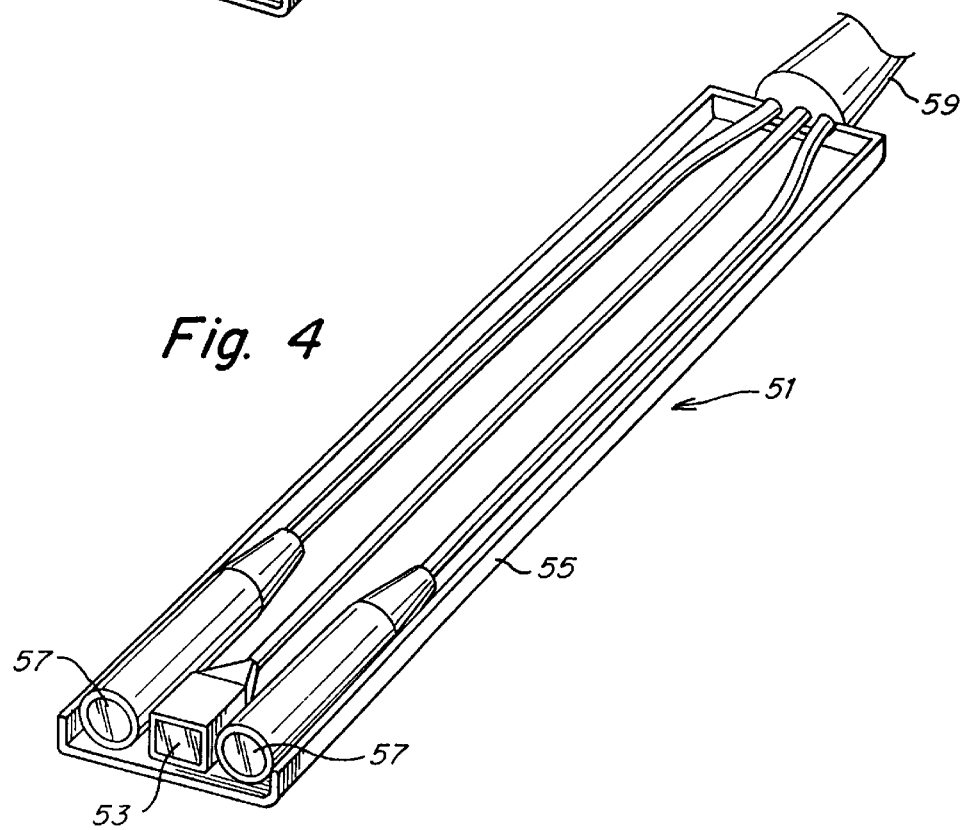
FIG. 4 is a perspective view of an alternative imaging sub-system that is suitable for use with the positioning system of the present invention to form a positionable camera system.

FIG. 4 is a perspective view of an alternative imaging sub-system that is also suitable for use with embodiments of the present invention. As shown in FIG. 4, the imaging sub-system 51 includes a CCD camera 53 attached to the distal end of an elongated sled 55. Also attached to the distal end of the sled 55 are two high intensity lights 57. A cable 59 connects the camera 53 to a display device (not shown) and the lights 57 to a source of electrical power. As in the imaging sub-system 5 described immediately above, cable 59 of imaging sub-system 51 can be formed by a flex circuit (e.g., 54 in FIG. 2). In this alternate embodiment, the imaging sub-system 51 is modified so that the CCD camera 53 and its associated lens (not shown) are placed at the distal end of the imaging sub-system 51 adjacent the clear seal 16. This improves the quality of the image that is provided by the camera system, and avoids many of the drawbacks associated with the use of optical fibers, such as their expense, their susceptibility to damage, and the faceting of the image that can result from the use of such optical fibers. Because the CCD camera 53 is mounted adjacent the distal end of the sled 55, imaging sub-system 51 may be preferred where image quality is a more significant factor than minimizing the size of the distal end of the camera system.

As should be appreciated by those skilled in the art, when the imaging sub-systems 5 and 51 are used in conjunction with positioning device 10, the dimensions of the elongated sled (i.e., sled 19 in FIG. 3 and sled 55 in FIG. 4) can be minimized to increase the degree of motion that is obtainable with the remotely positionable camera system. Alternatively, the lens and lights (e.g., lights 57 in FIG. 4) can be mounted to the CCD camera (e.g., CCD camera 53 in FIG. 4), and the CCD camera and lights can be connected to the flexible portion 54 of shaft 68 (FIG. 2). This reduces the size of the imaging sub-system and thereby increases the degree of motion that is obtainable with the remotely positionable camera system.

A second embodiment of a pressure control system 80 is shown in FIG. 5. Elements depicted in FIG. 5 having reference designators that are the same as those used in FIG. 2 have the same or similar function. As in FIG. 2, the positioning device 10 is not shown. Pressure control system 80 includes a handle 82 in which one or more fluid reservoirs are contained in a manner similar to that of the embodiment of FIG. 2. Pressure control system 80 includes two pairs of buttons 84, 86 and 92, 94 for directing the positioning of the positioning device 10 by inserting and removing the fluid into the fluid channels 18. Buttons 84 and 86 are ergonomically designed for use by a right-handed person, while buttons 92 and 94 are ergonomically designed for use by a left handed person. Buttons 84 and 92 are used to force fluid into the fluid channels 18 of the positioning device 10 while buttons 86 and 94 are used to permit the fluid to ebb from the fluid channels 18 of the positioning device 10. As depicted in FIG. 5, orifices 88 and 90 have a similar purpose and function to those of orifices 42 and 44 depicted in FIG. 2; that is, they are used to insert or remove fluid into the reservoir(s) of the pressure control system. Tips 50a' and 50b' serve a similar purpose as tips 50a and 50b that are depicted in FIG. 2. In fact, although not visible in FIG. 5, pressure control system 80 includes tips 50a and 50b. Together, tips 50a and 50a' (respectively on the left and right sides of the grip) are used to force fluid into the fluid channels 18 of the positioning device 10 while tips 50b and 50b' are used to permit fluid to ebb from the fluid channels 18 of the camera housing 10. Accordingly, in use, openings 20a and 20b (FIG. 1) are aligned with tips 50a and 50b, and openings 20a' and 20b' are aligned with tips 50a' and 50b'.

Figure 6:
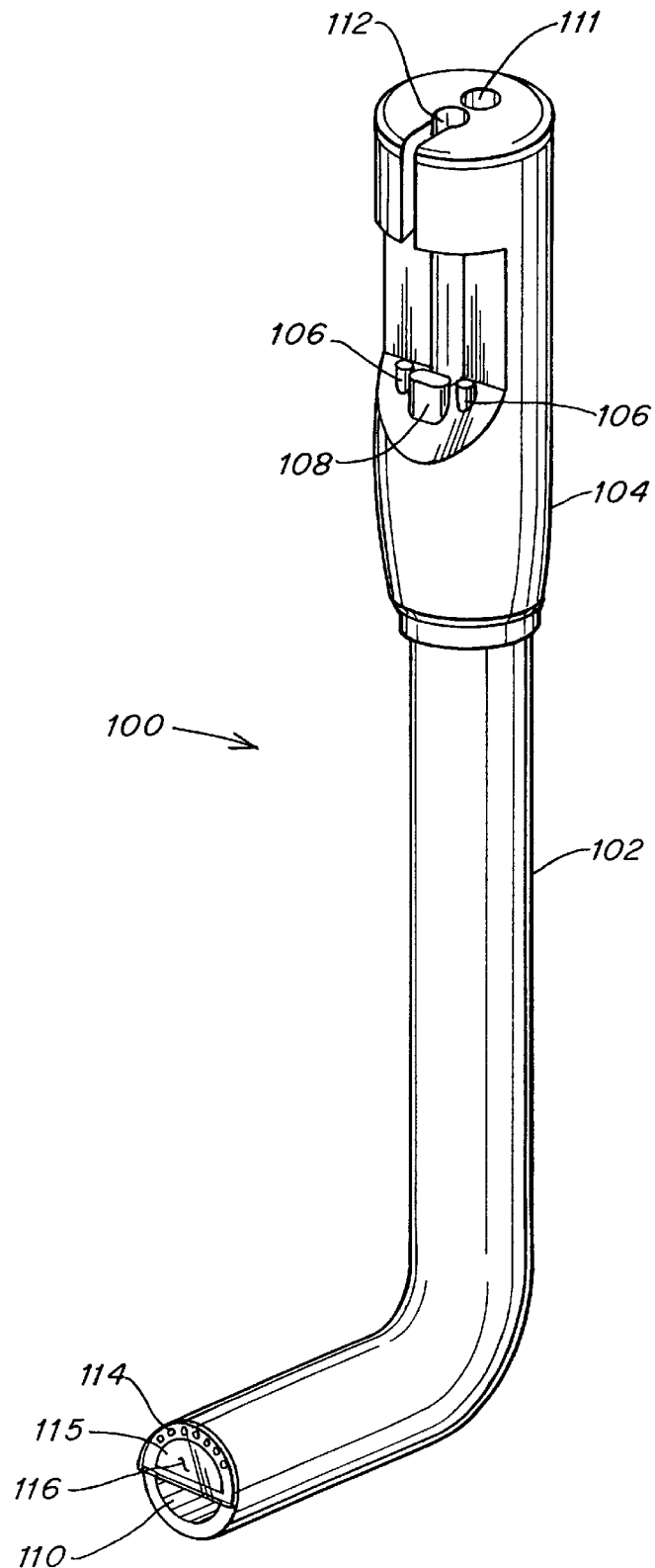
FIG. 6 is a perspective view of a controllable directional positioning system according to another embodiment of the present invention that integrates a controllable positioning device and a pressure control system into a single unit.
Figure 7:
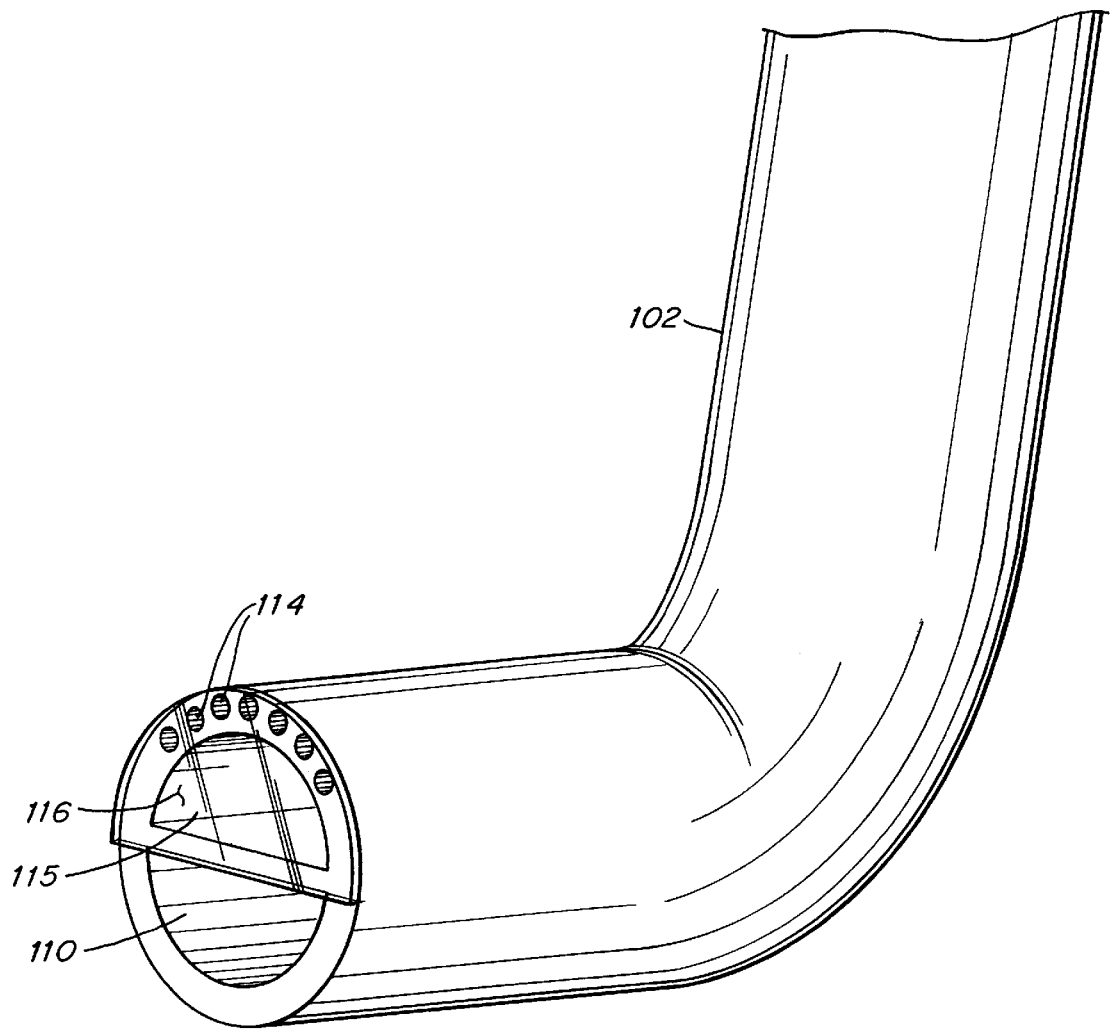
FIG. 7 is a detailed perspective view of the distal end of the controllable directional positioning system of FIG. 6.
Figure 8:
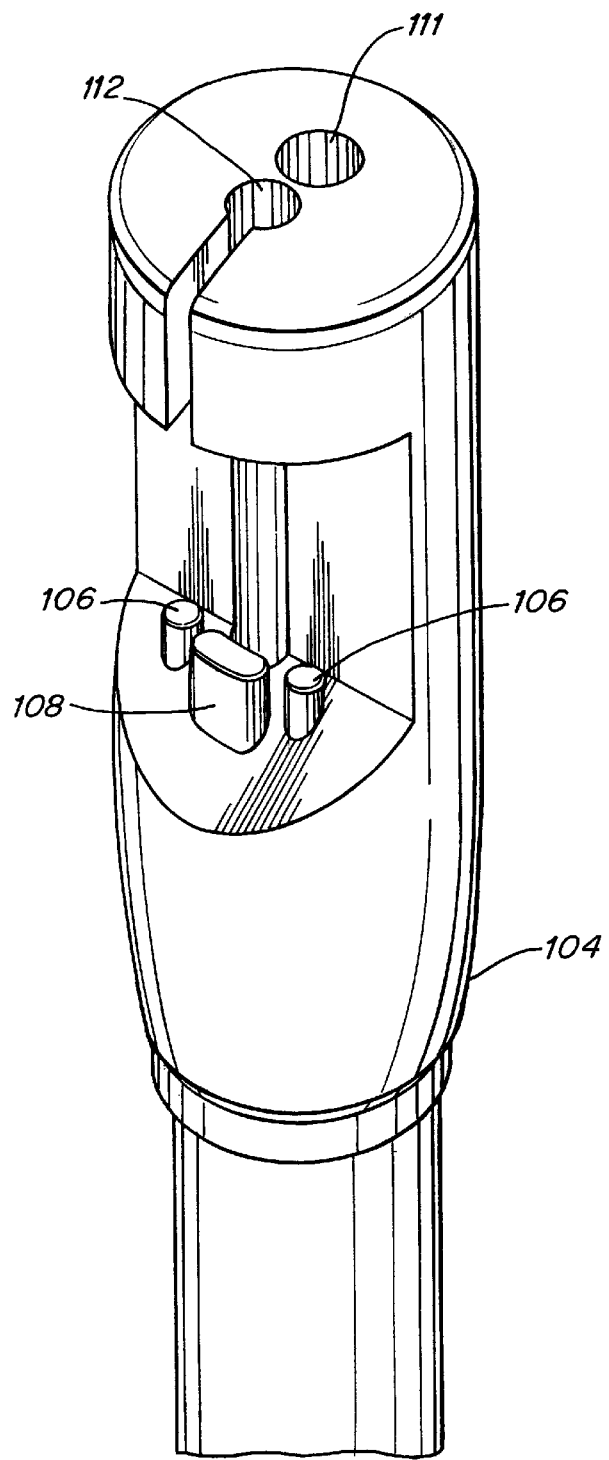
FIG. 8 is a detailed perspective view of the proximal end of the controllable directional positioning system of FIG. 6.

FIGS. 6, 7, and 8 illustrate a controllable directional positioning system according to another embodiment of the present invention, in which the controllable positioning device and the pressure control system are integrated into a single unit. This embodiment of the positioning system is particularly well suited for use with an endoscope for performing a wide variety of surgical and diagnostic procedures. As shown in FIG. 6, the positioning system 100 includes a controllable positioning device 102 and a pressure control system 104 in a single integrated unit. In one embodiment, the positioning device 102 and the pressure control system 104 can each be made from materials, such as plastic, that can be provided in a sterile condition and disposed of after use. The positioning device 102 and the pressure control system 104 can be formed as separate devices and then bonded together, or alternatively they may molded as a single unit.

The distal end of the positioning device 102 includes at least one longitudinally oriented fluid channel 114. In the embodiment shown in FIG. 6, the at least one fluid channel 114 includes a number of longitudinally oriented fluid channels that are disposed around a portion of the circumference of the device 102, although it should be appreciated that a single fluid channel can be employed. Alternatively, a number of fluid channels can be spaced about the entire circumference of the positioning device 102, or disposed around a different portion of the device. Although fluid channel 114 is shown as extending through the distal end of the positioning device 102, it should be appreciated that the distal end of the fluid channel is closed or sealed. The proximal end of the fluid channel 114, adjacent the pressure control system 104, is open to receive fluid.

In the embodiment shown in FIG. 6, the positioning device 102 includes two separate channels in addition to the fluid channels; that is, an instrument channel 115 and a working channel 110. The instrument channel 115 is open at the proximal end of the positioning device 102 and is adapted to mate with an instrument channel 112 in the pressure control system 104. Instrument channel 112 extends through the pressure control system 104 to the proximal end of the control system. Instrument channel 115 is sealed at the distal end of the positioning device 102 by an optically clear window 116. Because the instrument channel 115 is separated from the working channel 110 in the positioning device 102 and sealed by window 116, surgical instruments inserted into the instrument channel 115 need not be sterile. This is advantageous when the surgical instrument inserted into the instrument channel 115 is an endoscope, for reasons discussed above.

Working channel 110 is open at both the distal end and the proximal end of the positioning device 102. The proximal end of the positioning device 102 is adapted to mate with a working channel 111 in the pressure control system 104. Because working channel 110 is open at both ends, one or more surgical instruments can be inserted therein for manipulation of a surgical site. Such manipulation can be viewed using the endoscope inserted in the instrument channel 115.

Pressure control system 104 includes two pump triggers 106 and a release trigger 108. In a manner similar to that described above with respect to FIG. 2, actuating either one of pump triggers 106 forces fluid into the fluid channels 114 and actuating release trigger 108 removes fluid from the fluid channels 114. Fluid reservoirs (not shown) can be disposed within the body of the pressure control system 104. In the embodiment shown in FIG. 6, two pump triggers 106 are provided to facilitate operation of the positioning system 100 by both left-handed and right-handed operators.

FIG. 7 shows a more detailed view of the distal end of the positioning device 102 of FIG. 6. As shown in FIG. 7, the working channel 110 and the instrument channel 115 can be integrally formed within the body of the positioning device 102 so that they are separated by the body.

FIG. 8 shows a more detailed view of the proximal end of the pressure control system 104. As noted above, the pressure control system can include two pump triggers 106 to facilitate use by left-handed and right-handed operators. In particular, when the pressure control system 104 is held in the palm of the right hand, the right most pump trigger 106 is more easily manipulated by the thumb of the operator, and when held in the palm of the left hand, the left most pump trigger 106 is more easily manipulated. However, it should be appreciated that the present invention is not limited to the particular number or arrangement of trigger controls described herein, as other arrangements may be provided. Furthermore, the integrated embodiment of the controllable directional positioning system is not limited to two channels (i.e., instrument channel 115 and working channel 110), as an instrument channel or working channel can be used alone.

As described above, camera control systems of the present invention permit the remote viewing of objects, even when those objects are located at the end of a convoluted passageway. In one aspect of the invention, the camera control system can be used in a medically sterile environment, such as in a hospital operating room, as an endoscopic device. When the positioning device is disposable, the device may also be used in locations where equipment for sterilizing devices is not present. Of course, the device can also be used in sterile environments other than the medical field, and in non-sterile environments as well.

The remote positioning device of the present invention can also be used for numerous non-medical applications, a few of which are described briefly below. However, it should be appreciated that the following examples are by no means exhaustive, as numerous other applications will be readily occur to those skilled in the art. For example, the embodiments of the present invention can be employed in semiconductor wafer fabrication, where even a small amount of contamination by dust can destroy the yield of a manufacturing line. To inspect the wafer fabrication apparatus, the ability to view remote locations without impacting the cleanliness of the apparatus is a great benefit. Furthermore, because of the relatively small size of the remotely controllable camera system, embodiments of the present invention can be used to view areas that are inaccessible to the naked eye, or which would be dangerous to view with the naked eye (for example, due to the caustic chemicals and gases used in the semiconductor fabrication process).

Similarly, in the development of space or telescopic equipment, the ability to view remote locations without contamination is a significant benefit, as even the smallest amount of contamination can jeopardize the entire mission.

The present invention can be used to inspect the condition of remote areas of an aircraft wing for stress fractures, etc, without damage to the structure itself.

In addition, as discussed above, the positioning device of the present invention can be used to remotely position many types of tools, and is not limited to positioning a camera. In particular, where the distal end of the positioning device 10 (FIG. 1) is not sealed by transparent seal 16, the positioning device 10 can be use to remotely position many different types of tools and is not limited solely to use with medical instruments.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A positioning device, comprising:

a body having a first un-stressed configuration and at least one fluid channel to receive a fluid, the at least one fluid channel being constructed and arranged to transform the body of the positioning device from the first un-stressed configuration to a second configuration when fluid is forced into the at least one fluid channel; and a hand-held pressure control system that is in fluid communication with the at least one fluid channel and that alters a pressure of the fluid forced into the at least one fluid channel, the hand-held pressure control system having a body that includes
 a reservoir for storing the fluid and an opening that is in fluid communication with the reservoir, and
 a control, coupled to the opening, that allows the fluid to pass through the opening and return to the reservoir when the control is in a first state;

wherein the control forces the fluid from the reservoir and through the opening when the control is in a second state; and wherein the hand-held pressure control system includes a bi-directional valve coupled to the control.

2. A positioning device, comprising:

a body having a first un-stressed configuration and at least one fluid channel to receive a fluid, the at least one fluid channel being constructed and arranged to transform the body of the positioning device from the first un-stressed configuration to a second configuration when fluid is forced into the at least one fluid channel; and a hand-held pressure control system that is in fluid communication with the at least one fluid channel and that alters a pressure of the fluid forced into the at least one fluid channel, the hand-held pressure control system having a body that includes
 a reservoir for storing the fluid and an opening that is in fluid communication with the reservoir, and
 a control, coupled to the opening, that allows the fluid to pass through the opening and return to the reservoir when the control is in a first state;

wherein the reservoir includes a penetrable seal through which the fluid can be injected into the reservoir.

3. A positioning device, comprising:

a body having a first un-stressed configuration and at least one fluid channel to receive a fluid, the at least one fluid channel being constructed and arranged to transform the body of the positioning device from the first un-stressed configuration to a second configuration when fluid is forced into the at least one fluid channel; and a hand-held pressure control system that is in fluid communication with the at least one fluid channel and that alters a pressure of the fluid forced into the at least one fluid channel, the hand-held pressure control system having a body that includes
 a reservoir for storing the fluid and an opening that is in fluid communication with the reservoir, and
 a control, coupled to the opening, that allows the fluid to pass through the opening and return to the reservoir when the control is in a first state;

wherein the reservoir includes a second opening that is in fluid communication with the reservoir, and wherein the body of the hand-held positioning system includes a second opening that that allows the fluid to pass through the second opening from the reservoir when the at least one control is in a second state.

4. A positioning device, comprising:

a body having a first un-stressed configuration and at least one fluid channel to receive a fluid, the at least one fluid channel being constructed and arranged to transform the body of the positioning device from the first un-stressed configuration to a second configuration when fluid is forced into the at least one fluid channel; and a hand-held pressure control system that is in fluid communication with the at least one fluid channel and that alters a pressure of the fluid forced into the at least one fluid channel;

wherein the hand-held pressure control system has a body that includes:
 a first reservoir for storing the fluid;
 a first opening that is in fluid communication with the first reservoir;
 a first control, coupled to the first opening, that allows the fluid to pass through the opening and return to the first reservoir when the control is in a first state;
 a second reservoir for storing the fluid;
 a second opening that is in fluid communication with the second reservoir; and
 a second control, coupled to the second opening, that forces the fluid from the second reservoir through the second opening when the second control is in the first state.

\* \* \* \* \*